US006656947B2

(12) United States Patent
Husbands et al.

(10) Patent No.: US 6,656,947 B2
(45) Date of Patent: Dec. 2, 2003

(54) ANTIDEPRESSANT AZAHETEROCYCLYLMETHYL DERIVATIVES OF 2,3-DIHYDRO-1,4-DIOXINO[2,3-F]QUINAZOLINE

(75) Inventors: George E. M. Husbands, Berwyn, PA (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/127,926

(22) Filed: Apr. 23, 2002

(65) Prior Publication Data

US 2002/0183341 A1 Dec. 5, 2002

Related U.S. Application Data

(60) Provisional application No. 60/286,573, filed on Apr. 26, 2001.

(51) Int. Cl.$^7$ .................. C07D 49/04; C07D 49/056; A61K 31/505; A61K 31/445; A61P 25/24
(52) U.S. Cl. ........................... 514/267; 544/250
(58) Field of Search .................. 544/250; 514/267

(56) References Cited

U.S. PATENT DOCUMENTS

| | | | |
|---|---|---|---|
| 5,318,988 A | 6/1994 | Schohe-Loop et al. ..... | 514/458 |
| 5,371,094 A | 12/1994 | Heine et al. ................ | 514/323 |
| 5,741,789 A | 4/1998 | Hibschman et al. ........ | 514/210 |
| 5,756,532 A | 5/1998 | Stack et al. ................. | 514/411 |
| 5,869,490 A | 2/1999 | Stack ........................... | 514/255 |

FOREIGN PATENT DOCUMENTS

| | | |
|---|---|---|
| WO | WO 95/07274 | 3/1995 |
| WO | WO 97/23485 | 7/1997 |
| WO | WO 98/16530 | 4/1998 |
| WO | WO 98/40386 | 9/1998 |

OTHER PUBLICATIONS

Frederic Saudou et al., Med. Chem. Res., 1994, 16–84, 4.
Marcel Hibert et al., J. Med. Chem., 1988, 1087–1093, 31.

*Primary Examiner*—Bruck Kifle
(74) *Attorney, Agent, or Firm*—Woodcock Washburn LLP

(57) ABSTRACT

Compounds of the formula:

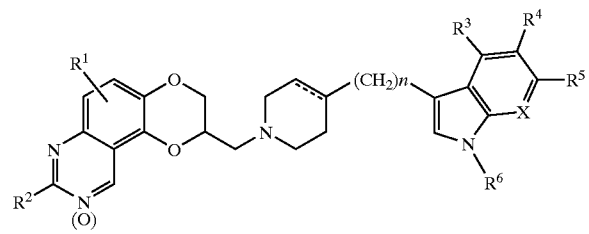

useful for the treatment of depression and other diseases such as obsessive compulsive disorder, panic attacks, generalized anxiety disorder, social anxiety disorder, sexual dysfunction, eating disorders, obesity, addictive disorders caused by ethanol or cocaine abuse and related illnesses

22 Claims, No Drawings

ANTIDEPRESSANT AZAHETEROCYCLYLMETHYL DERIVATIVES OF 2,3-DIHYDRO-1,4-DIOXINO[2,3-F]QUINAZOLINE

This application claims priority from provisional application Ser. No. 60/286,573, filed on Apr. 26, 2001, the entire disclosure of which is hereby incorporated by reference.

BACKGROUND OF THE INVENTION

Major depression is a serious health problem affecting more than 5% of the population, with a life-time prevalence of 15–20%.

Selective serotonin reuptake inhibitors have produced significant success in treating depression and related illnesses and have become among the most prescribed drugs. They nonetheless have a slow onset of action, often taking several weeks to produce their full therapeutic effect. Furthermore, they are effective in fewer than two-thirds of patients.

Serotonin selective reuptake inhibitors (SSRIs) are well known for the treatment of depression and other conditions. SSRIs work by blocking the neuronal reuptake of serotonin, thereby increasing the concentration of serotonin in the synaptic space, and thus increasing the activation of postsynaptic serotonin receptors.

However, although a single dose of an SSRI can inhibit the neuronal serotonin transporter which would be expected to increase synaptic serotonin, long-term treatment is required before clinical improvement is achieved.

It has been suggested that the SSRIs increase the serotonin levels in the vicinity of the serotonergic cell bodies and that the excess serotonin activates somatodendritic autoreceptors, $5-HT_{1A}$ receptors, causing a decrease in serotonin release in major forebrain areas. This negative feedback limits the increment of synaptic serotonin that can be induced by antidepressants.

A $5-HT_{1A}$ antagonist would limit the negative feedback and should improve the efficacy of the serotonin reuptake mechanism. (Perez, V., et al., The Lancet, 349:1594–1597 (1997)). Such a combination therapy would be expected to speed up the effect of the serotonin reuptake inhibitor.

Thus, it is highly desirable to provide improved compounds which both inhibit serotonin reuptake and which are antagonists of the $5-HT_{1A}$ receptor.

DESCRIPTION OF THE INVENTION

In accordance with this invention, there is provided a group of novel compounds of the formula:

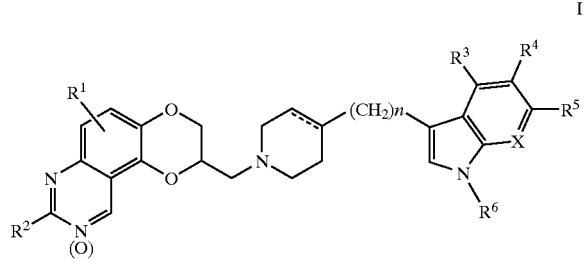

I wherein $R^1$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ is hydrogen or alkyl of 1 to 6 carbon atoms;

A dotted line represents an optional double bond;

(O) represents optional oxidation;

X is $CR^7$ or N; and n is an integer 0, 1 or 2;

or a pharmaceutically acceptable salt thereof.

In some preferred embodiments $R^1$ is hydrogen, hydroxy, halo, cyano, trifluoromethyl, alkyl of one to six carbon atoms or alkoxy of one to six carbon atoms. In still other embodiments of the present invention $R^1$ is hydrogen.

In other embodiments of the invention $R^2$ is hydrogen, hydroxy, halo, alkyl of one to six carbon atoms, amino, mono- or di-alkylamino in which each alkyl group has one to six carbon atoms. Still more preferred is when $R^2$ is hydrogen or lower alkyl.

$R^3$, $R^4$, $R^5$ are independently selected from hydrogen, hydroxy, halo, cyano, carboxamido, alkyl of one to six carbon atoms, and alkoxy of one to six carbon atoms in some embodiments of the present invention. $R^3$, $R^4$ and $R^5$ are still more preferably independently halogen and hydrogen.

$R^6$ is preferably hydrogen in some embodiments of the present invention.

Preferred embodiments of the invention are those in which $R^1$ is hydrogen, hydroxy, halo, cyano, trifluoromethyl, alkyl of one to six carbon atoms or alkoxy of one to six carbon atoms; $R^2$ is hydrogen, hydroxy, halo, alkyl of one to six carbon atoms, amino, mono- or di-alkylamino in which each alkyl group has one to six carbon atoms; $R^3$, $R^4$ and $R^5$ are independently selected from hydrogen, hydroxy, halo, cyano, carboxamido, alkyl of one to six carbon atoms, and alkoxy of one to six carbon atoms; n is an integer 0 or 1.

More preferred are compounds in which $R^1$ is is hydrogen, hydroxy, halo, cyano, trifluoromethyl, alkyl of one to six carbon atoms or alkoxy of one to six carbon atoms, $R^2$ is hydrogen or alkyl of one to six carbon atoms, $R^3$, $R^4$ and $R^5$ are independently selected from hydrogen, halo and cyano, X is $CR^7$, $R^7$ is hydrogen, halo or cyano, $R^6$ is hydrogen, n is 0 and the dotted line represents a double bond.

Still more preferred embodiments of the invention are those in which $R^1$ is hydrogen, $R^2$ is hydrogen or lower alkyl, and $R^3$, $R^4$ and $R^5$ are independently selected from hydrogen and halogen, X is $CR^7$, $R^7$ is hydrogen or halogen, $R^6$ is hydrogen and n is an integer 0.

This invention relates to both the R and S stereoisomers of the aminomethyl-2,3-dihydro-1,4-dioxino[2,3-f] quinazolines, as well as to mixtures of the R and S stereoisomers. Throughout this application, the name of the product of this invention, where the absolute configuration of the aminomethyl-2,3-dihydro-1,4-dioxino[2,3-f]quinazolines is not indicated, is intended to embrace the individual R and S enantiomers as well as mixtures of the two. In some preferred embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

It is further recognized that tautomers of the claimed compounds may exist, for instance, when $R^2$ is hydroxy, a tautomeric form may exist. Tautomeric forms of compounds of the present invention are thus encompassed herein.

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of the present invention include:
2-[(4-(5-fluoro-1H-indol-3-yl)-3,6-dihydropyridin-1(2H)-yl)methyl]-2,3-dihydro[1,4]dioxino[2,3-f]quinazoline;
2-[(4-(1H-indol-3-yl)-3,6-dihydropyridin-1(2H)-yl)methyl]-2,3-dihydro-[1,4]dioxino[2,3-f]quinazoline;
2-[(4-(1H-indol-3-yl)-3,6-dihydropyridin-1(2H)-yl)methyl]-8-methyl-2,3-dihydro[1,4]dioxino[2,3-f]quinazoline 9-oxide;
2-[(4-(1H)-indol-3-yl)-3,6-dihydropyridin-1(2H)-yl)methyl]-8-methyl-2,3-dihydro[1,4]dioxino[2,3-f]quinazoline; and 2-[(4-(1H-indol-3-yl)-3,6-dihydropyridin-1(2H)-yl)methyl]-8-ethyl-2,3-dihydro[1,4]dioxino[2,3-f]quinazoline and pharmaceutically acceptable salts thereof.

The present invention also provides certain compounds of Formula II which are useful for the preparation of compounds of Formula I.

Thus, an intermediate of the formula

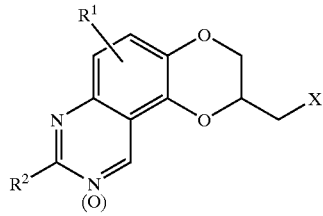

II wherein
$R^1$ is hydrogen, hydroxy, halo, cyano, carboxamido, carboalkoxy of two to six carbon atoms, trifluoromethy, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

X is halogen, hydroxy, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms;

(O) represents optional oxidation;
useful for the production of agents for the treatment of depression and other central nervous system disorders, are provided.

Specific intermediates of the invention include:
2,3-Dihydro[1,4]dioxino[2,3-f]quinazolin-2-ylmethyl 4-methylbenzene-sulfonate.
(8-Methyl-2,3-dihydro[1,4]dioxino-[2,3-f]quinazolin-2-yl)methyl 4-methylbenzene sulfonate;
(8-Methyl-9-oxo-2,3-dihydro[1,4]dioxino-[2,3-f]-quinazolin-2-yl)methyl 4-methylbenzene sulfonate; and
(8-Ethyl-2,3-dihydro[1,4]dioxino-[2,3-f]-quinazolin-2-yl)-methyl 4-methylbenzene sulfonate.

The 2-azaheterocyclylmethyl-2,3-dihydro-1,4-dioxino[2,3-f]quinazolines of the invention are prepared as illustrated in Schemes I through III. Specifically, the appropriately substituted nitroguaiacol (1) is alkylated with allyl bromide in the presence of a suitable base such as sodium hydride to produce (2) and then demethylated by a reagent such as sodium hydroxide. The resulting 4-nitro-2-allyloxyphenol (3) is then alkylated with glycidyl tosylate or an epihalohydrin in the presence of a base such as sodium hydride to produce (4) and heated in a high boiling solvent such as mesitylene or xylene to effect both rearrangement of the allyl group and cyclization of the dioxan ring. The resulting primary alcohol (5) is converted to the tosylate by reaction with p-toluenesulfonyl chloride in the presence of a tertiary amine or pyridine, or alternatively to a halide by reaction with carbon tetrabromide or carbon tetrachloride in combination with triphenylphosphine to produce. The allyl side chain is then Scheme I

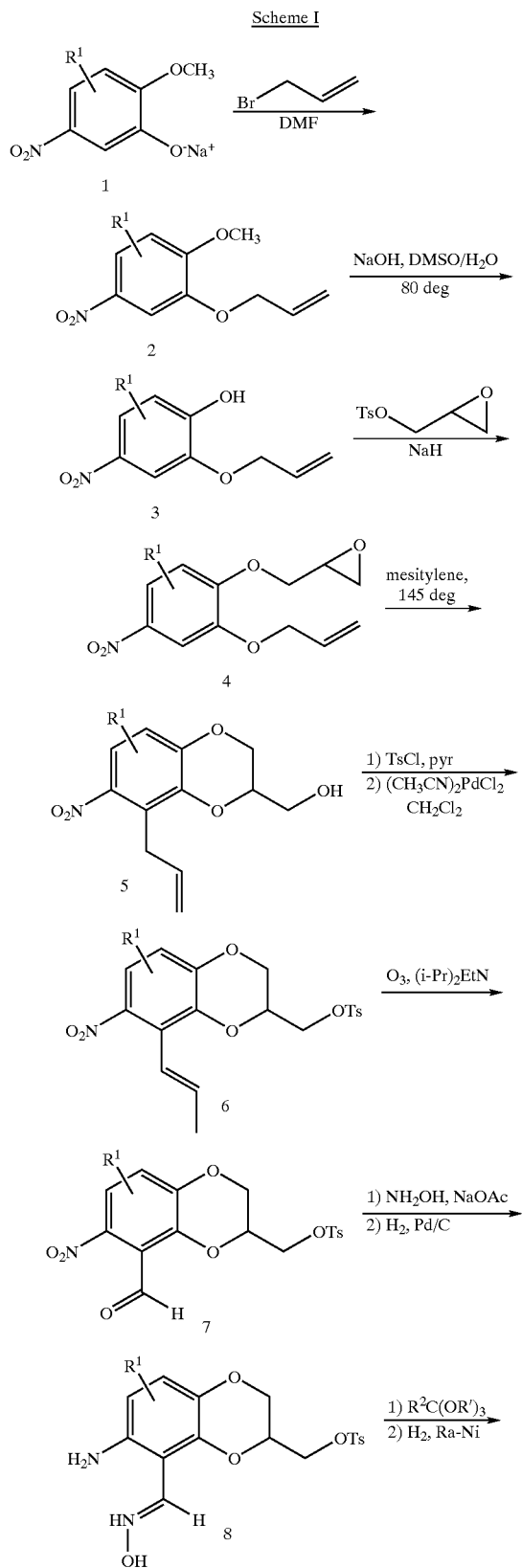

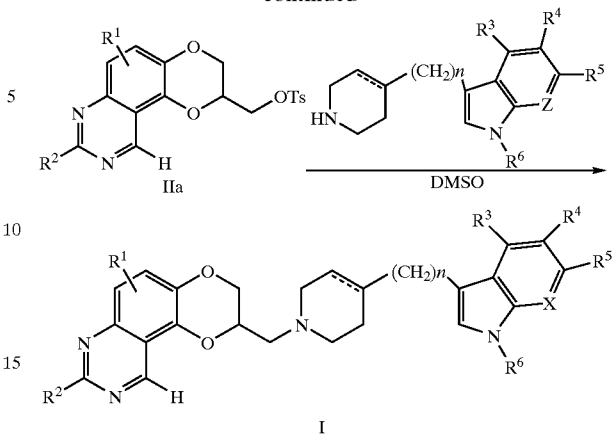

isomerized by treatment with catalytic bis-acetonitrile palladium (II) chloride in refluxing methylene chloride or benzene to produce (6) and cleaved to the corresponding o-nitrobenzaldehyde (7) by treatment with ozone followed by diisopropylethylamine or by catalytic osmium tetroxide in the presence of sodium periodate. The aldehyde is converted to the oxime (8) by treatment with hydroxylamine hydrochloride in the presence of a suitable base such as sodium acetate and the nitro group reduced to the amine by hydrogenation over palladium on carbon. Cyclization to the quinazoline N-oxide (IIa) is effected by treatment at reflux with the appropriate ortho ester according to the method of Ostrowski (Heterocycles, vol. 43, No. 2, p. 389, 1996). The quinazoline N-oxide may be reduced to the quinazoline by a suitable reducing agent such as hydrogen over Raney-nickel. Alternatively, an extended period of reflux in the ortho ester gives the reduced quinazoline directly via a disproportionation reaction and the 2,3-dihydro-1,4-dioxino[2,3-f]quinazoline-2-methyltosylate or halide may be isolated by column chromatography. Replacement of the tosylate or halide with the appropriately substituted azaheterocycle in some high boiling solvent such as dimethyl sulfoxide gives the title compounds of the invention.

The o-nitrobenzaldehyde used in the chemistry described above may be alternatively prepared as shown in Scheme II. The appropriate mono-allylated catechol (10) is elaborated with glycidyl tosylate as described above to produce (11) and rearranged in refluxing mesitylene. Cyclization to the benzodioxan methanol (12) is Scheme II

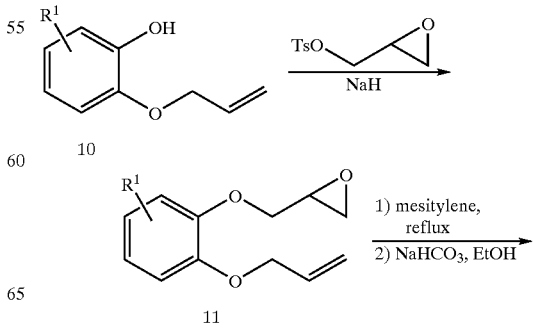

Scheme III

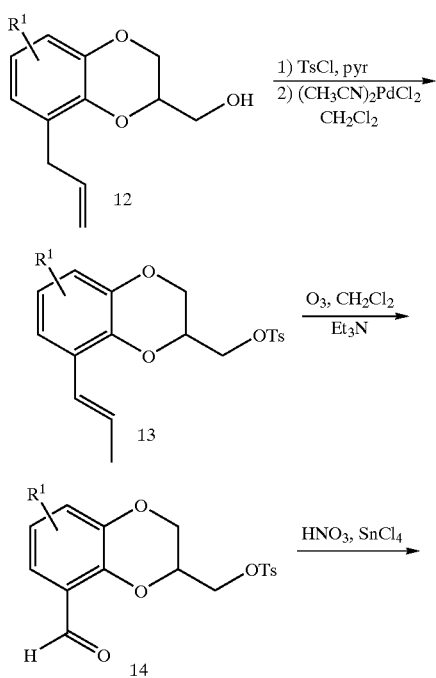

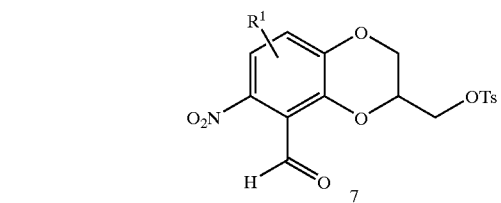

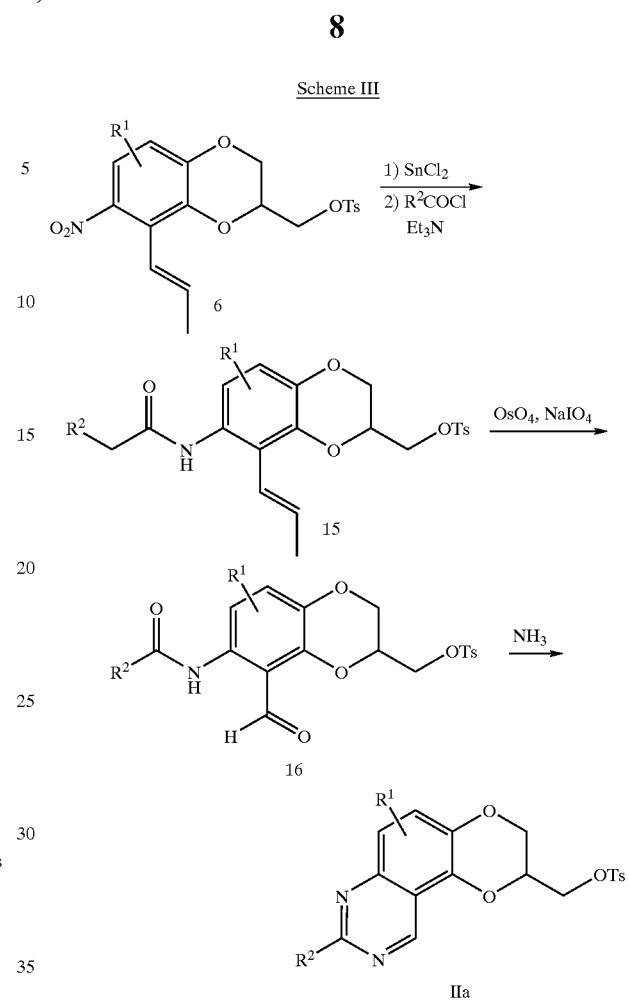

effected by treatment with sodium bicarbonate in ethanol and the alcohol is converted to the tosylate or halide as described above. After rearrangement of the double bond by treatment with catalytic bis-acetonitrile palladium (II) chloride in refluxing methylene chloride to produce (13) and cleavage with ozone or osmium tetroxide/sodium periodate as described above, the resulting aldehyde (14) is regioselectively nitrated with a combination of nitric acid and tin (IV) chloride to produce (7).

The compounds of the invention may be alternatively prepared from the rearranged olefin described above by the method outlined in Scheme III. The nitro olefin (6) is first reduced to the aniline by treatment with a suitable reducing agent such as stannous chloride dihydrate in refuxing ethyl acetate and the resulting amine acylated with the appropriate acyl halide or anhydride. The olefin (15) is then converted to the aldehyde (16) by cleavage with catalytic osmium tetroxide in the presence of excess sodium periodate. Cyclization directly to the 2,3-dihydro-1,4-dioxino[2,3-f]quinazoline-2-methyltosylate or halide (IIa) is effected by treatment of the amido aldehyde with ammonia and replacement of the tosylate or halide with the appropriately substituted azaheterocycle in some high boiling solvent such as dimethyl sulfoxide as described above gives the title compounds of the invention.

The guaiacols, catechols and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzene-sulfonate or tosylate (for the R enantiomer) in place of epihalohydrin or racemic glycidyl tosylate in the procedures above.

A protocol similar to that used by Cheetham et. al. (Neuropharmacol. 32:737, 1993) was used to determine the affinity of the compounds of the invention for the serotonin transporter. The compound's ability to displace $^3$H-paroxetine from male rat frontal cortical membranes was determined using a Tom Tech filtration device to separate bound from free $^3$H-paroxetine and a Wallac 1205 Beta Plate® counter to quantitate bound radioactivity. $K_i$'s thus determined for standard clinical antidepressants are 1.96 nM for fluoxetine, 14.2 nM for imipramine and 67.6 nM for zimelidine. A strong correlation has been found between $^3$H-paroxetine binding in rat frontal cortex and $^3$H-serotonin uptake inhibition.

High affinity for the serotonin 5-HT$_{1A}$ receptor was established by testing the claimed compound's ability to displace [$^3$H] 8-OHDPAT (dipropylamino-tetralin) from the 5-HT$_{1A}$ serotonin receptor following a modification of the procedure of Hall et al., J. Neurochem. 44, 1685 (1985) which utilizes CHO cells stably transfected with human 5-HT$_{1A}$ receptors.

The 5-HT$_{1A}$ affinities for the compounds of the invention are reported below as K$_i$'s.

Antagonist activity at 5-HT$_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-HT$_{1A}$ receptors was determined. Agonists produce an increase in binding whereas antagonists produce no increase but rather reverse the effects of the standard agonist 8-OHDPAT. The test compound's maximum inhibitory effect is represented as the I$_{max}$, while its potency is defined by the IC$_{50}$.

The results of the three standard experimental test procedures described in the preceding three paragraphs were as follows:

| Compound | 5-HT Transporter Affinity KI (nM) | 5-HT$_{1A}$ Receptor Affinity KI (nM) | 5-HT$_{1A}$ Function IC$_{50}$ (nM) (I$_{max}$) |
|---|---|---|---|
| Example 1 | 2.24 | 51.53 | 499.0 (94.0) |
| Example 2 | 2.87 | 15.02 | 379.0 (100) |
| Example 3 | 4.64 | 25.58 | 440.0 (94.0) |
| Example 4 | 2.26 | 2.40 | 116.0 (100) |
| Example 5 | 4.25 | 8.27 | 209.0 (100) |

Like the antidepressants fluoxetine, paroxetine and sertraline, the compounds of this invention have the ability to potently block the reuptake of the brain neurotransmitter serotonin. They are thus useful for the treatment of depression and other diseases commonly treated by the administration of serotonin selective reuptake inhibitor (SSRI) antidepressants. Moreover, the compounds of this invention have potent affinity for and antagonist activity at brain 5-HT$_{1A}$ serotonin receptors. Recent clinical trials employing drug mixtures (eg, fluoxetine and pindolol) have demonstrated a more rapid onset of antidepressant efficacy for a treatment combining SSRI activity and 5-HT$_{1A}$ antagonism (Blier and Bergeron, 1995; F. Artigas et. al., 1996; M. B. Tome et. al., 1997). The compounds of the invention are thus exceedingly interesting and useful for treating depressive illnesses.

Hence, the compounds of this invention are combined serotonin reuptake inhibitors/5-HT$_{1A}$ antagonists and are useful for the treatment of conditions related to or affected by the reuptake of serotonin and by the serotonin 1A receptor, such as depression (including but not limited to major depressive disorder, childhood depression and dysthymia), anxiety, panic disorder, post-traumatic stress disorder, premenstrual dysphoric disorder (also known as pre-menstrual syndrome), attention deficit disorder (with and without hyperactivity), obsessive compulsive disorder (including trichotillomania), social anxiety disorder, generalized anxiety disorder, obesity, eating disorders such as anorexia nervosa, bulimia nervosa, vasomotor flushing, cocaine and alcohol addiction, sexual. dysfunction (including premature ejaculation), and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol gave m.p. 93–94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

INTERMEDIATE 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$ Calc'd: C, 57.37; H, 5.21; N, 5.58. Found: C, 57.50; H, 5.21; N, 5.43.

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$ Calc'd: C, 57.37; H, 5.21; N, 5.58. Found: C, 57.26; H, 5.20; N, 5.35.

INTERMEDIATE 5

Toluene-4-sulfonic Acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$ Calc'd: C, 56.29; H, 4.72; N, 3.45. Found: C, 56.13; H, 4.58; N, 3.44.

INTERMEDIATE 6

{7-nitro-8-[1-propenyl]-2,3-dihydro-1,4-benzodioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$ Calc'd: C, 56.29; H, 4.72; N, 3.45. Found: C, 56.12; H, 4.64; N, 3.39.

INTERMEDIATE 7

(8-Formyl-7-nitro-2,3-dihydro-1,4-benzodioxin-2-yl) methyl 4-methylbenzenesulfonate {(2R)-7-Nitro-8-[1-propenyl]-2,3-dihydro-1,4-benzodioxin-2-yl}methyl 4-methylbenzenesulfonate (10.5 g, 25.9 mmole) dissolved in 400 mL of methylene chloride was treated with excess ozone at −78° C. Diisopropylethylamine (11.5 mL, 66.0 mmole) was then added dropwise over 30 min and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ(2 H); doublet 7.62 δ(1 H); doublet 7.4 δ(2 H); doublet 7.0 δ(1 H); multiplet 4.4–4.6 δ(2 H); multiplet 4.2 δ(3 H); singlet 2.4 δ(3 H).

INTERMEDIATE 8

Toluene-4-sulfonic Acid 8-(hydroximino-methyl)-7-nitro-2,3-dihydro-1,4-benzodioxin-2-ylmethyl) ester

[(2R)-8-Formyl-7-nitro-2,3-dihydro-1,4-benzodioxin-2-yl]methyl 4-methylbenzene sulfonate (8.0 g, 20 mmole) was dissolved in a mixture of methanol (280 mL) and water (30 mL). Hydroxylamine hydrochloride (2.0 g, 28 mmole) and sodium acetate (2.5 g) were added, and the mixture stirred at room temperature under nitrogen for 18 hours. The solvent was removed and replaced with ethyl acetate. The solution was then washed with water and saturated sodium chloride solution, dried over anhydrous magnesium sulfate, then filtered and concentrated under vacuum. The solid obtained was filtered with petroleum ether and air-dried, yield 6.0 g (72%). A sample was recrystallized from isopropyl alcohol and yielded the (R)-enantiomer of the title compounds as a white solid, m.p. 132–133° C.

Elemental Analysis for: $C_{17}H_{16}N_2O_8S$ Calc'd: C, 50.00; H, 3.95; N, 6.86. Found: C, 49.63; H, 3.99; N, 6.69.

INTERMEDIATE 9

Toluene-4-sulfonic Acid 7-amino-8-(hydroximino-methyl)-2,3-dihydrobenzo[1,4]dioxin-2-ylmethyl ester Toluene-4-sulfonic acid [2R]-8-(hydroximino-methyl)-7-nitro-2,3-dihydro-1,4-benzodioxin-2-yl methyl ester (4.0 g, 9.8 mmole) was hydrogenated for 4 hours in ethanol (570 mL) in a Parr apparatus with 1.0 g of 10% palladium on charcoal as catalyst. The catalyst was filtered and the filtrate evaporated giving a green solid (3.2 g, 86%). A sample was crystallized for isopropanol yielding the (R)-enantiomer of the title compound as a light green solid, m.p. 164–166° C.

Elemental Analysis for: $C_{17}H_{18}N_2O_6S$ Calc'd: C, 53.96; H, 4.79; N, 7.4. Found: C, 53.16; H, 4.85; N, 7.4.

INTERMEDIATE 10

2,3-Dihydro[1,4]dioxino[2,3-f]quinazolin-2-ylmethyl-4-methylbenzenesulfonate

Toluene-4-sulfonic acid (2R)-7-amino-8-(hydroximino-methyl)-2,3-dihydrobenzo[1,4]dioxin-2-ylmethyl ester (3.0 g, 7.9 mmole) was suspended in triethyl orthoformate under nitrogen, brought to a rapid boil and refluxed for 18 hours. The reaction mixture was cooled and the solvent evaporated. The residue was dissolved in methylene chloride (100 mL) and the solution obtained was washed with saturated sodium chloride (100 mL), dried over magnesium sulfate and evaporated to a brown gum (2.7 g) which contained several impurities. Chromatography on silica gel using 1% methanol in chloroform and then 3% methanol in chloroform as eluants gave 0.9 g (30%) of the (R)-enantiomer of the title compound as an oil. $^1$H(DMSO-d$_6$) singlet, 9.01 δ(1 H); singlet, 9.19 δ(1 H); doublet, 7.75 δ(2 H); doublet, 7.60 δ(1 H); doublet, 7.50 δ(1 H) doublet, 7.30 δ(2 H); multiplet, 4.75 δ(1 H); double doublet, 4.51 δ(1 H); double doublet, 4.46 δ(1 H) double doublet: 4.32 δ(1 H); double doublet, 4.22 δ(1 H); singlet, 2.32 δ(3 H).

EXAMPLE 1

2-[(4-(5-Fluoro-1H-indol-3-yl)-3,6-dihydropyridin-1 (2H)-yl)methyl]-2,3-dihydro[1,4]dioxino[2,3-f] quinazoline (2R)-2,3-Dihydro-1,4-dioxino[2,3-f]quinazolin-2-ylmethyl-4-methylbenzenesulfonate (800 mg, 3.7 mmole) was dissolved in a mixture of DMF/THF 1:1 v/v (30 mL) and 5-fluoro-3-(1,2,3,6-tetrahydro-4-pyridinyl)-1H-indole (800 mg, 4 mmole) added, followed by the addition of sodium bicarbonate (1.0 gm, 9.4 mmole) and the mixture was refluxed under nitrogen for 18 hours. The solvent was evaporated under vacuum and the residue partitioned between methylene chloride and water. The organic phase was separated, washed with water and saturated sodium chloride solution, dried over magnesium sulfate and evaporated to a foam. Treatment of this foam with 3% methanol in chloroform yielded 320 mg (35%) of the (S)-enantiomer of the title compound as a yellow crystalline hemihydrate, m.p. 233–235° C.

Elemental Analysis for: $C_{24}H_{21}FN_4O_2.0.5H_2O$ Calc'd: C, 67.75; H, 5.21; N, 13.17. Found: C, 67.88; H, 5.2; N, 13.08.

EXAMPLE 2

2-[(4-(1H-Indol-3-yl)-3,6-dihydropyridin-1(2H)-yl)methyl]-2,3-dihydro[1,4]dioxino[2,3-f]quinazoline (2R)-2,3-Dihydro[1,4]dioxino[2,3-f]quinazolin-2-ylmethyl-4-methylbenzenesulfonate (300 mg, 1.4 mmole) and 3-(1,2,3,6-tetrahydro-4-pyridinyl)-1H-indole (300 mg, 0.80 mmole) were dissolved in a mixture of DMF and THF (1:1 v/v, 20 mL). Sodium bicarbonate (600 mg) was added and the reaction mixture refluxed under nitrogen for 18 hours. The reaction mixture was cooled and the solvent evaporated under vacuum. The residue was partitioned between methylene chloride and water. The organic phase was separated, washed with water and saturated sodium chloride solution, dried over magnesium sulfate and evaporated yielding a gum (490 mg) containing several impurities. Chromatography on silica gel using 1% methanol in chloroform and then 3% methanol in chloroform as eluants yielded 40 mg (12%) of the (S)-enantiomer of the title compound as an off-white crystalline solid, m.p. 204–207° C. (hemihydrate).

Elemental Analysis for: $C_{24}H_{22}N_4O_2.0.5H_2O$ Calc'd: C, 70.74; H, 5.68; N, 13.75. Found: C, 71.08; H, 5.46; N, 13.68.

EXAMPLE 3

2-[(4-(1H-Indol-3-yl)-3,6-dihydropyridin-1(2H)-yl)methyl]-8-methyl-2,3-dihydro[1,4]dioxino[2,3-f]quinazoline 9-oxide Toluene-4-sulfonic acid (2R)-7-amino-8-(hydroximinomethyl)-2,3-dihydro-1,4-benzodioxin-2-ylmethyl ester (1.0 g, 2.6 mmole) was suspended in triethyl orthoacetate (20 mL) and the mixture refluxed under nitrogen for two hours. The reaction mixture was cooled, and the solvent evaporated under vacuum. The crude residue (1.5 g) was dissolved in a mixture of THF/DMF 1:1 v/v (25 mL) and 3-(1,2,3,6-tetrahydro-4-pyridinyl)1H-indol (1.5 g, 7.5 mmole) and sodium bicarbonate (1.5 g) added. The mixture was refluxed under nitrogen for 20 hours. The reaction mixture was cooled, and the solvent evaporated. The residue was partitioned between methylene chloride and water. The layers were separated. The organic phase was washed with water and saturated sodium chloride solution, dried over magnesium sulfate and the solvent evaporated under vacuum. The crude residual oil (2.7 g) was chromatographed on silica gel using 1% methanol in chloroform, followed by 2% and 3% methanol in chloroform as eluants, to give the (S)-enantiomer of the title compound as a yellow solid (40 mg), m.p. 118–192° C.

Elemental Analysis for: $C_{25}H_{24}N_4O_3.H_2O$ Calc'd: C, 67.25; H, 5.87; N, 12.55. Found: C, 66.70; H, 5.60; N, 11.80.

EXAMPLE 4

2-[(4-(1H-Indol-3-yl)-3,6-dihydropyridin-1(2H)-yl)methyl]-8-methyl-2,3-dihydro[1,4]dioxino[2,3-f]quinazoline Toluene-4-sulfonic acid (2R)-7-amino-8-(hydroximinomethyl)-2,3-dihydrobenzo[1,4]dioxin-2-yl methyl ester (1.5 g, 3.9 mmole) was suspended in triethyl orthoacetate (20 mL) and the mixture refluxed for 18 hours. The reaction mixture was cooled, and the solvent evaporated. The residue was dissolved in methylene chloride, and the solution obtained was washed with saturated sodium chloride solution, dried over magnesium sulfate and evaporated to a brown gum. This was chromatographed on a silica gel column using 1% methanol in chloroform, followed by 3% methanol in chloroform. The desired intermediate (2R)-(8-methyl-2,3-dihydro[1,4]dioxino-[2,3-f]-quinazolin-2-yl) methyl 4-methyl-benzene sulfonate (300 mg, 20%) was obtained. It was then dissolved in a mixture of DMF/THF, 1:1 v/v (20 mL), 3-(1,2,3,6-tetrahydro-4-pyridinyl)-1H-indole (250 mg, 1.2 mmole) and sodium bicarbonate (500 mg, 4.7 mmole) added, and the mixture refluxed for 18 hours. The reaction mixture was cooled, the solvent evaporated, and the residue partitioned between methylene chloride and water. The layers were separated. The organic phase was washed with water and saturated sodium chloride solution, dried over magnesium sulfate and evaporated under vacuum, yielding a crude oil (420 mg). This residue was chromatographed on silica gel using first 2% methanol in chloroform and then 3% methanol in chloroform to give the (S)-enantiomer of the title compound as a yellow solid, m.p. 198–202° C. (monohydrate).

Elemental Analysis for: $C_{25}H_{24}N_4O_2.H_2O$ Calc'd: C, 69.75; H, 6.08; N, 11.14. Found: C, 69.74; H, 5.70; N, 11.14.

EXAMPLE 5

2-[(4-(1H-Indol-3-yl)-3,6-dihydropyridin-1(2H)-yl)methyl]-8-ethyl-2,3-dihydro[1,4]dioxino[2,3-f]quinazoline Toluene-4-sulfonic acid (2R)-7-amino-8-(hydroximinomethyl)2,3-dihydrobenzo[1,4]dioxin-2-ylmethyl ester (1.0 g, mmole) was suspended in triethyl orthopropionate (20 mL) and the mixture refluxed under nitrogen for 18 hours. The reaction mixture was cooled and the solvent evaporated under vacuum. The residue was dissolved in methylene chloride, the solution washed with saturated sodium chloride solution, dried over magnesium sulfate and the solvent evaporated to a gum (1.5 g). This residue was dried under vacuum and dissolved in a mixture of DMF/THF 1:1 v/v (100 mL). 3-(1,2,3,6-Tetrahydro-4-pyridinyl)-1H-indole (1.2 g, 6 mmole) and sodium bicarbonate (3.0 g) were added and the mixture refluxed under nitrogen for 20 hours. The reaction mixture was cooled, and the solvent evaporated under vacuum. The residue was partitioned between methylene chloride and water. The layers were separated. The organic phase was washed with water and saturated sodium chloride solution, dried over magnesium sulfate and the solvent removed under vacuum. The crude oil obtained (2.0 g) was chromatographed on silica gel using 2% methanol in chloroform, followed by 3% methanol in chloroform as eluants to give the (S)-enantiomer of the title compound (52 mg), m.p. 203–211° C.

Elemental Analysis for: $C_{26}H_{26}N_4O_2.0.75H_2O$ Calc'd: C, 70.97; H, 6.29; N, 12.73. Found: C, 70.99; H, 5.92; N, 12.60.

What is claimed is:

1. A compound of formula I

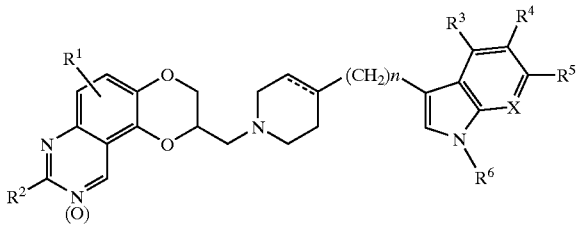

wherein
- $R^1$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- $R^2$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- $R^6$ is hydrogen or alkyl of 1 to 6 carbon atoms;
- A dotted line represents an optional double bond;
- (O) represents optional oxidation;
- X is $CR^7$ or N; and
- n is an integer 0, 1 or 2;

or a pharmaceutically acceptable salt thereof.

2. A compound of claim 1 wherein $R^1$ is hydrogen, hydroxy, halo, cyano, trifluoromethyl, alkyl of one to six carbon atoms or alkoxy of one to six carbon atoms.

3. A compound of claim 2 wherein $R^1$ is hydrogen.

4. A compound of claim 1 wherein $R^2$ is hydrogen, hydroxy, halo, alkyl of one to six carbon atoms, amino, mono- or di-alkylamino in which each alkyl group has one to six carbon atoms.

5. A compound of claim 4 wherein $R^2$ is hydrogen or lower alkyl.

6. A compound of claim 1 wherein $R^3$, $R^4$, $R^5$ are independently selected from hydrogen, hydroxy, halo, cyano, carboxamido, alkyl of one to six carbon atoms, and alkoxy of one to six carbon atoms.

7. A compound of claim 6 wherein $R^3$, $R^4$ and $R^5$ are independently selected from halogen and hydrogen.

8. A compound of claim 1 in which $R^1$ is hydrogen, hydroxy, halo, cyano, trifluoromethyl, alkyl of one to six carbon atoms or alkoxy of one to six carbon atoms; $R^2$ is hydrogen, hydroxy, halo, alkyl of one to six carbon atoms, amino, mono- or di-alkylamino in which each alkyl group has one to six carbon atoms; $R^3$, $R^4$ and $R^5$ are independently selected from hydrogen, hydroxy, halo, cyano, carboxamido, alkyl of one to six carbon atoms, and alkoxy of one to six carbon atoms; n is an integer 0 or 1; or a pharmaceutically acceptable salt thereof.

9. A compound of claim 1 in which $R^1$ is hydrogen, hydroxy, halo, cyano, trifluoromethyl, alkyl of one to six carbon atoms or alkoxy of one to six carbon atoms, $R^2$ is hydrogen or alkyl of one to six carbon atoms, $R^3$, $R^4$ and $R^5$ are independently selected from hydrogen, halo and cyano, $R^6$ is hydrogen, X is $CR^7$, $R^7$ is hydrogen, halo or cyano, n is 0 and the dotted line represents a double bond; or a pharmaceutically acceptable salt thereof.

10. A compound of claim 1 in which $R^1$ is hydrogen, $R^2$ is hydrogen or lower alkyl, and $R^3$, $R^4$ and $R^5$ are independently selected from hydrogen and halogen, X is $CR^7$, $R^7$ is hydrogen or halogen, $R^6$ is hydrogen and n is an integer 0.

11. The compound of claim 1 which is 2-[(4-(5-fluoro-1H-indol-3-yl)-3,6-dihydropyridin-1(2H)-yl)methyl]-2,3-dihydro[1,4]dioxino[2,3-f]quinazoline or a pharmaceutically acceptable salt thereof.

12. The compound of claim 1 which is 2-[(4-(1H-indol-3-yl)-3,6-dihydro-pyridin-1(2H)-yl)methyl]-2,3-dihydro[1,4]dioxino[2,3-f]quinazoline or a pharma-ceutically acceptable salt thereof.

13. The compound of claim 1 which is 2-[(4-(1H-indol-3-yl)-3,6-dihydro-pyridin-1(2H)-yl)methyl]-8-methyl-2,3-dihydro[1,4]dioxino[2,3-f]-quinazoline 9-oxide or a pharmaceutically acceptable salt thereof.

14. The compound of claim 1 which is 2-[(4-(1H-indol-3-yl)-3,6-dihydro-pyridin-1(2H)-yl)methyl]-8-methyl-2,3-dihydro[1,4]dioxino[2,3-f]-quinazoline or a pharmaceutically acceptable salt thereof.

15. The compound of claim 1 which is 2-[(4-(1H-indol-3-yl)-3,6-dihydro-pyridin-1(2H)-yl)methyl]-8-ethyl-2,3-dihydro[1,4]dioxino[2,3-f]quinazoline or a pharmaceutically acceptable salt thereof.

16. A compound of the formula

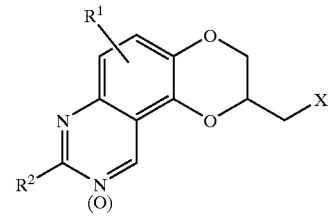

wherein
- $R^1$ is hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- $R^2$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;
- X is halogen, hydroxy, alkylsulfonate of 1 to 6 carbon atoms, trifluoromethanesulfonate or benzenesulfonate, in which the benzene ring is optionally substituted with halogen, nitro, trifluoromethyl, cyano, alkyl of 1 to 6 carbon atoms or alkoxy of 1 to 6 carbon atoms;
- (O) represents optional oxidation.

17. A compound of claim 16 which is selected from:
- 2,3-Dihydro[1,4]dioxino[2,3-f]quinazolin-2-ylmethyl 4-methylbenzene-sulfonate;
- (8-Methyl-2,3-dihydro[1,4]dioxino-[2,3-f]-quinazolin-2-yl)methyl 4-methyl-benzene sulfonate;

(8-Methyl-9-oxo-2,3-dihydro[1,4]dioxino-[2,3-f]-quinazolin-2-yl)methyl 4-methylbenzene sulfonate; and (8-Ethyl-2,3-dihydro[1,4]dioxino-[2,3-f]-quinazolin-2-yl)-methyl 4-methyl-benzene sulfonate.

18. A method of treating a subject suffering from a condition selected from the group consisting of depression, anxiety, panic disorder, post-traumatic stress disorder, premenstrual dysphoric disorder, attention deficit disorder, obsessive compulsive disorder, social anxiety disorder, generalized anxiety disorder, obesity, anorexia nervosa, bulimia nervosa, vasomotor flushing, alcohol addiction, and sexual dysfunction which comprises providing to the subject suffering from said condition, a therapeutically effective amount of a compound of formula I

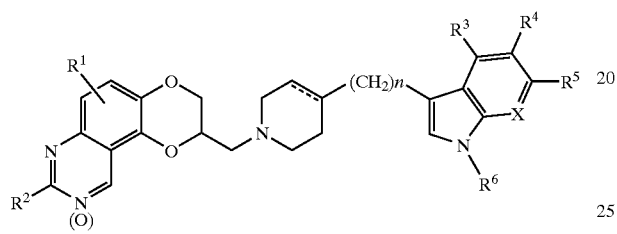

wherein $R^1$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ is hydrogen or alkyl of 1 to 6 carbon atoms;

A dotted line represents an optional double bond;

(O) represents optional oxidation;

X is $CR^7$ or N; and n is an integer 0, 1 or 2;

or a pharmaceutically acceptable salt thereof.

19. The method of claim 18 wherein the condition is depression.

20. The method of claim 18 wherein the condition is obsessive compulsive disorder, panic attacks, generalized anxiety disorder or social anxiety disorder.

21. The method of claim 18 wherein the subject is a human.

22. A pharmaceutical composition comprising a compound of formula I

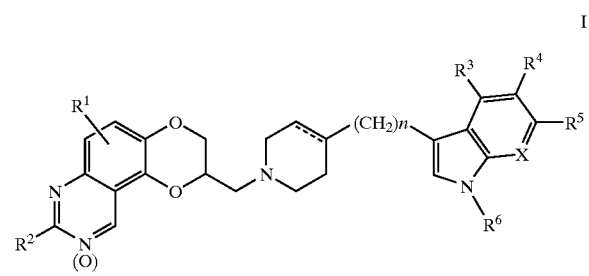

wherein $R^1$, $R^3$, $R^4$, $R^5$ and $R^7$ are, independently, hydrogen, hydroxy, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, hydroxy, halo, cyano, carboxamido, carboalkoxy of two to six carbon atoms, alkyl of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^6$ is hydrogen or alkyl of 1 to 6 carbon atoms;

A dotted line represents an optional double bond;

(O) represents optional oxidation;

X is $CR^7$ or N; and n is an integer 0, 1 or 2;

or a pharmaceutically acceptable salt thereof, and a pharmaceutically acceptable carrier or excipient.

* * * * *